(12) United States Patent
Dholakia et al.

(10) Patent No.: US 9,816,802 B2
(45) Date of Patent: Nov. 14, 2017

(54) OPTICAL COHERENCE TOMOGRAPHY

(75) Inventors: Kishan Dholakia, Fife (GB); Mario Ettore Giardini, Fife (GB)

(73) Assignee: UNIVERSITY COURT OF THE UNIVERSITY OF ST ANDREWS

(*) Notice: Subject to any disclaimer, the term of this patent is extended or adjusted under 35 U.S.C. 154(b) by 0 days.

(21) Appl. No.: 13/643,036

(22) PCT Filed: Jun. 2, 2011

(86) PCT No.: PCT/GB2011/000841
§ 371 (c)(1),
(2), (4) Date: Jan. 9, 2013

(87) PCT Pub. No.: WO2011/151628
PCT Pub. Date: Dec. 8, 2011

(65) Prior Publication Data
US 2013/0107273 A1    May 2, 2013

(30) Foreign Application Priority Data

Jun. 2, 2010   (GB) .................................. 1009233.6

(51) Int. Cl.
*G01B 9/02*     (2006.01)
*G01N 21/47*    (2006.01)

(52) U.S. Cl.
CPC ....... *G01B 9/02091* (2013.01); *G01N 21/474* (2013.01); *G01N 21/4795* (2013.01); *G01N 2021/4709* (2013.01)

(58) Field of Classification Search
CPC . G01B 9/02; C09K 19/00; A61B 1/04; G01N 21/00; G01S 1/20
USPC ......................... 356/479; 428/1.1; 369/53.23
See application file for complete search history.

(56) References Cited

U.S. PATENT DOCUMENTS

| | | | |
|---|---|---|---|
| 5,665,957 A * | 9/1997 | Lee et al. .................... | 369/53.23 |
| 6,115,127 A * | 9/2000 | Brodeur ................. | G01B 17/00 356/432 |
| 6,592,950 B1* | 7/2003 | Toshima et al. ............... | 428/1.1 |
| 2004/0169857 A1* | 9/2004 | Acosta ................. | G01N 21/278 356/328 |
| 2004/0246490 A1 | 12/2004 | Wang | |
| 2006/0109478 A1* | 5/2006 | Tearney et al. ............... | 356/479 |
| 2007/0008545 A1 | 1/2007 | Feldchtein et al. | |
| 2007/0109553 A1 | 5/2007 | Feldchtein et al. | |

(Continued)

FOREIGN PATENT DOCUMENTS

WO    WO 2006/058049 A1    6/2006

OTHER PUBLICATIONS

Tearney et al.: "In Vivo Endoscopic Optical Biopsy with Optical Coherence Tomography"; Science, vol. 276, Jun. 27, 1997, pp. 2037-2039.

(Continued)

*Primary Examiner* — Jamil Ahmed
(74) *Attorney, Agent, or Firm* — Moore & Van Allen PLLC; W. Kevin Ransom

(57) ABSTRACT

An optical coherence tomography system comprising a light source (a) and a probe (e) that has a window at a front facing end. The window has an inner face (i) that has an anti-reflection surface and allows light from the source to pass through it, and an outer face (j) that reflects some of the light from the source and transmits some of the light to and from the sample (k). The reflected light acts as a reference.

23 Claims, 5 Drawing Sheets

(56) References Cited

U.S. PATENT DOCUMENTS

2008/0055603 A1    3/2008  Amazeen et al.
2011/0085161 A1*   4/2011  Thien .................... G01N 21/94
                                                        356/237.3

OTHER PUBLICATIONS

Tumlinson et al.: "Endoscope-tip interferometer for ultrahigh resolution frequency domain optical coherence tomography in mouse colon"; Optics Express, vol. 14, No. 5, Mar. 6, 2006, pp. 1878-1887.
Sergeev et al.: "In vivo endoscopic OCT imaging of precancer and cancer states of human mucosa"; Optics Express, vol. 1, No. 13, Dec. 22, 1997, pp. 432-440.
Tan et al.: "In-fiber common-path optical coherence tomography using a conical-tip fiber"; Optics Express, vol. 17, No. 4, Feb. 16, 2009, pp. 2375-2384.
Cairns et al.: P-58: Laser Speckle of Textured Surfaces: Towards High Performance Anti-Glare Surfaces; SID Symposium Digest of Technical Papers, vol. 38, No. 1, May 2007 pp. 407-409.
International Search Report for PCT/GB2011/000841, dated Aug. 19, 2011.
UK Search Report for GB1009233.6, dated Aug. 3, 2010.

\* cited by examiner a)

b)

a)

0 μm
150 μm
300 μm
450 μm
600 μm
750 μm
900 μm b)

OPTICAL COHERENCE TOMOGRAPHY

FIELD OF THE INVENTION

The present invention relates to a fiber based self-referenced and potentially self-aligning Fourier-domain optical coherence tomography optical configuration.

BACKGROUND OF THE INVENTION

Optical Coherence Tomography (OCT) systems are based on Michelson interferometers. Light from a low optical coherence (i.e. broadband) source is split into two arms. The length of one arm (the reference arm) is defined by a mirror. On the other arm the mirror is replaced by the sample that backscatters light into the interferometer. The light from the two arms is recombined, and only light that has been backscattered at a depth that matches the length of the reference arm within the coherence length of the source can interfere. Such coherence length is defined by the source spectral width, and is typically a few microns when the optical bandwidth is a few tens of nanometers.

By altering the optical length of the reference arm, for example by varying the reference mirror position, it is possible to explore scattering at different sample depths. In practice, the sample surface is typically scanned sequentially (e.g., by raster or conical scan), or in parallel (using an array of detectors), and the sample depth is probed by scanning the reference arm optical length (for example, by a mechanical scan), exploring a typical depth on the order of 2 mm. An alternative technique for depth scanning relies on the fact that the interferogram collected by scanning the optical length of the reference arm is effectively the Fourier transform of the spectrum collected on the interferometer output. Therefore, the reference arm can be kept fixed, and the interferometer output is connected to a spectrograph or a frequency-swept narrowband source is used to explore the spectrum sequentially. The backscattering profile is calculated as a Fourier transform of the spectrum. This is referred to as Fourier-domain Optical Coherence Tomography (FT-OCT).

OCT is intrinsically non-invasive and exhibits great potential in in-vivo measurements, where it complements more traditional technologies, such as ultrasound imaging, by employing a different contrast mechanism and by offering higher resolution, at the expense of a much lower penetration depth. The conceptual simplicity of the OCT probes, essentially consisting of optical coupling elements between a scattering medium and an interferometer arm, leads to endoluminal and enodocavitary medicine, such as endoscopy and laparoscopy, as a natural field of application. However, other applications are known, for example, in non-surgical medicine, and in the analysis of paint layers or varnished surfaces or wood.

When a remote probe head is desired, such as, for example, in endoscopic or laparoscopic applications, the probe needs to be connected to external light sources, to spectrometers and, often, to part of the interferometer. This leads to the necessity for optical fiber tethering of the distal end of the probe. If the coupling is performed through single mode fibers, very little light is collected. If multimode fibers are used, mode mixing, dispersion, curvature losses and curvature dependence of the optical pathlength of the probe need to be taken into consideration and, if necessary, compensated. Also, it may be desirable that the probe should be front-looking, as this would simplify endoscopy or laparoscopy.

Currently most probes are side looking and employ a version of a Michelson interferometer in which an arm is directly implemented on a side-looking probe tip, see for example Guillermo J. Tearney, Mark E. Brezinski,* Brett E. Bouma, Stephen A. Boppart, Costas Pitris, James F. Southern, James G. Fujimoto, In Vivo Endoscopic Optical Biopsy with Optical Coherence Tomography, Science 276 (1997) 2037-2039. In other cases, the reference arm is implemented in the tip either through a separate reflective element or using retroreflection from the back surface of the side window, as described in Alexandre R. Tumlinson, Jennifer K. Barton, Boris Považay, Harald Sattman, Angelika Unterhuber, Rainer A. Leitgeb, Wolfgang Drexler, Endoscope-tip interferometer for ultrahigh resolution frequency domain optical coherence tomography in mouse colon, Optics Express 14 (2006) 1878-1887. In both cases, in order to avoid a loss of field of view, the side window is curved and needs to be kept to a thickness of the order of 100 µm. Also as, in the state of the art, the reference arm is either separate from the sample arm or a curved reference is used, and so a complex and potentially non-scalable alignment of the probe elements is necessary.

A front looking probe has been proposed by A. M. Sergeev et al. This is described in the article *In vivo endoscopic OCT imaging of precancer and cancer states of human mucosa*, Optics Express 13 (1997) 433-440. This probe is based on a scanned Michelson interferometer at the proximal end of the endoscopic probe, coupled to a raster-scanning distal end. To keep the image clear from artifacts deriving from the reflection from the front window, the field of view is kept on a virtual plane well clear of the front window, and protruding a few millimeters into the free space in front of the endoscopic probe. This can make manipulation of the probe awkward.

Another fiber-based OCT system is described by K. M. Tan et al in "In-fiber common-path optical coherence tomography using a conical-tip fiber", Optics Express 17 (2009) 2375-2384. This fiber-based solution is incompatible with windows thicker than a few tens of µm, as the window thickness detracts from the depth of field.

SUMMARY OF THE INVENTION

According to the present invention, there is provided an optical coherence tomography system comprising a light source and a probe that has a window at a front facing end, wherein the window has an inner face that has an anti-reflection surface and allows light from the source to pass through it, and an outer face that reflects some of the light from the source, the reflected light acting as a reference, and transmits some of the light to and from the sample.

The present invention provides a front-looking probe protected by a window that has inner and outer faces, which together allow reflection of a reference signal and sample signal transmission. The nature of these faces means the window can be of a thickness that allows it to be placed in contact with the sample without danger of breaking and causing injury. The probe is self-aligning and simple.

The anti-reflection surface may be an anti-Newton surface.

The outer face may be treated to so that the reference signal is a scattered signal. The outer face may be roughened, thereby to cause the scattered signal. The scattered signal may be small compared to the transmitted signal. The scattered light may be less than 50% of the transmitted light.

The probe may include one or more optical elements. The optical element may comprise at least one focusing means. The focusing means may comprise at least one lens.

The system may include an optical fiber for coupling light into and out of the probe. The end of the fiber may be shaped to focus light in the probe.

The fiber may be treated to avoid or reduce reflections from the end that is coupled with the probe. The fiber end may be coated with an anti-reflection material.

An anti-reflection window may be provided for coupling the fiber end to the probe. The anti-reflection window and fiber may be coupled using glue or an index matching material, for example a gel.

BRIEF DESCRIPTION OF THE DRAWINGS

Various aspects of the invention will now be described by way of example only and with reference to the accompanying drawings, of which:

FIG. 4 (b) is an image taken at 1050 μm, and heavily filtered to allow visualization of the skin outline, indicated by the arrow.

DETAILED DESCRIPTION OF THE DRAWINGS

Figure 1:
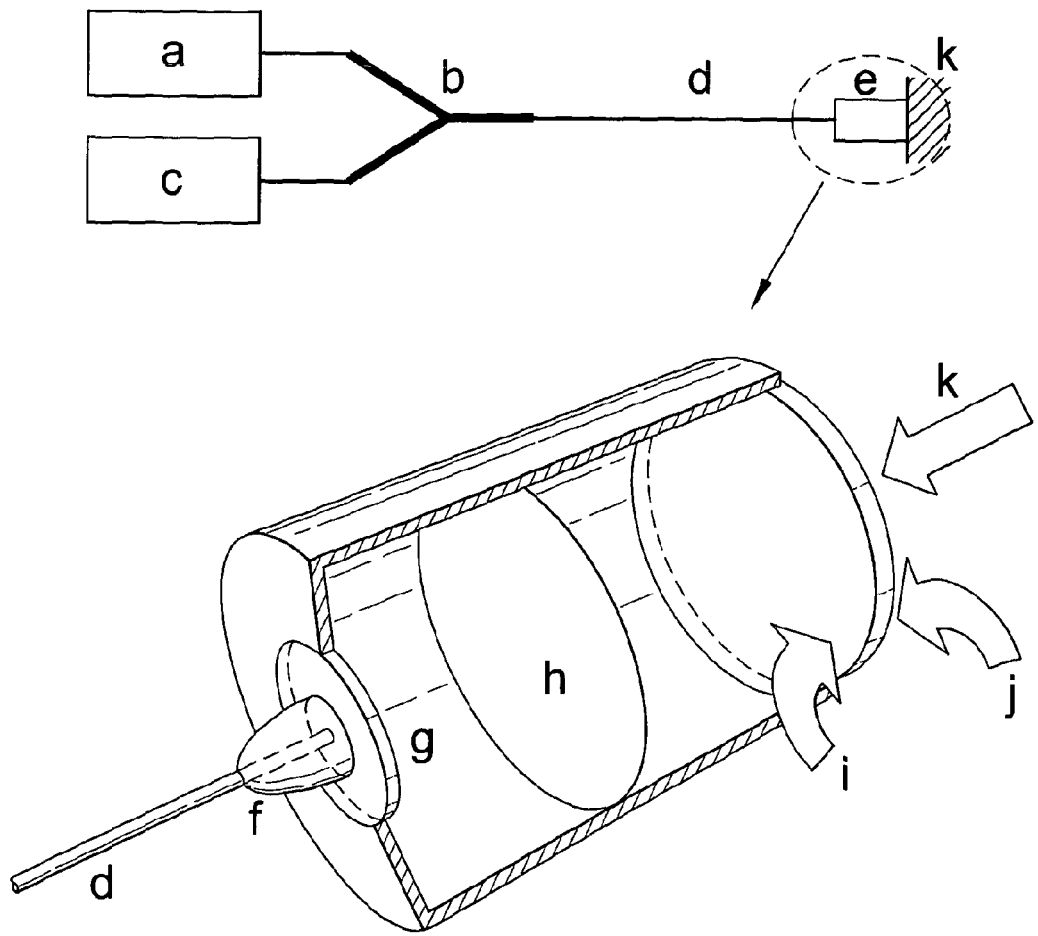
FIG. 1 is a schematic view of an OCT system, with an expanded view of a probe head.

FIG. 1 shows a fiber based OCT system. This has an optical source a, and a spectrometer c, each of which is connected to an optical fiber. The optical fibers are fed via a beam splitter/combiner b to an optical fiber tether d, which is connected to a probe head e. The probe head is generally cylindrical and has windows at either end. The end of the fiber tether d contacts a first one of the probe windows g. This has an anti-reflection coating on its internal face. To improve the contact between the fiber and the first window, an index-matching gel f is used.

Inside the probe head and between the two windows is a focusing lens h. At the sample end of the probe is a front window. To avoid reflections from the back of the window causing etaloning effects and secondary references masking the OCT signal, the internal window surface i is treated to be anti-reflection. The anti-reflection surface could be coated with an anti-reflection material. In a preferred example, the internal surface has undergone a treatment known as "anti-Newton". This surface i is engineered to suppress face-face interference while imposing minimal scattering losses. Anti-Newton surfaces are described by D. R. Cairns, P. Evans, in Laser speckle of textured surfaces: *Towards high performance anti-glare surfaces*, SID International Symposium, Digest of technical papers 38 (2007) 407-409. The external surface of the front window j is polished and optionally treated with a coating that is partially reflective to light from the source. The coating may be, for example, a metallic layer or a dielectric stack, as well known in the art.

In use, the probe is positioned with the external surface j directly in close proximity or directly in contact with the sample k that is being investigated. Light from the source passes through the anti-reflection inner face i and onto the outer face j, where some of the light is reflected back and used as a reference, and some passes into the sample k. Light backscattered from the sample k subsequently passes through surface j and is transmitted to the detector where it can be processed. Using reflections from the front surface j of the window as a reference means that the reference and the sample backscattering are intrinsically co-aligned for collection by the coupling optics to the common arm of the splitter.

The system of FIG. 1 has been tested. In the test device, the optical source used was a telecommunication-grade low-cost LED optical source (850 nm). This was coupled through a 63 μm core fiber to a 2-to-1 multimode 50%-50% splitter/combiner. The reference and sample arms of the OCT interferometer shared the common fiber of the splitter, whose output was spliced to a second ST-connectorized 63 μm-core fiber connected to the probe head. To avoid swamping the probe head signal into a background coming from the reflection from the connector termination, the ST connector was coupled through an index-matching gel to a broadband near-infrared optimized anti-reflection coated window. The optical power output at the window was nominally 50 μW. The light was then focused through a 25 mm focal length, 23 mm diameter biconvex lens on a 1:1.6 throw (fiber-side NA 0.27) onto the front face of an output window. The fiber-side window surface is "anti-Newton" and is engineered to completely suppress face-face interference while imposing minimal (on the order of 10%) scattering losses (25 DA 00, Comar Instruments, UK).

The second arm of the two way splitter, capturing the light coming both from the common reference and sample arm, was fed into a spectrometer (Shamorock i303, Andor, Ireland), configured to 60 nm bandwidth and 0.15 nm resolution, and a spectrum was captured at 16-bit digitalization by a front-illuminated CCD camera, with exposure times varying from 20 to 200 ms, Fourier transformed (thus implementing a FD-OCT configuration) and acquired for post-processing. The whole head was mounted on a motorized translator, controlled directly by the spectrometer driver software, which takes care of the system synchronization.

Figure 2:
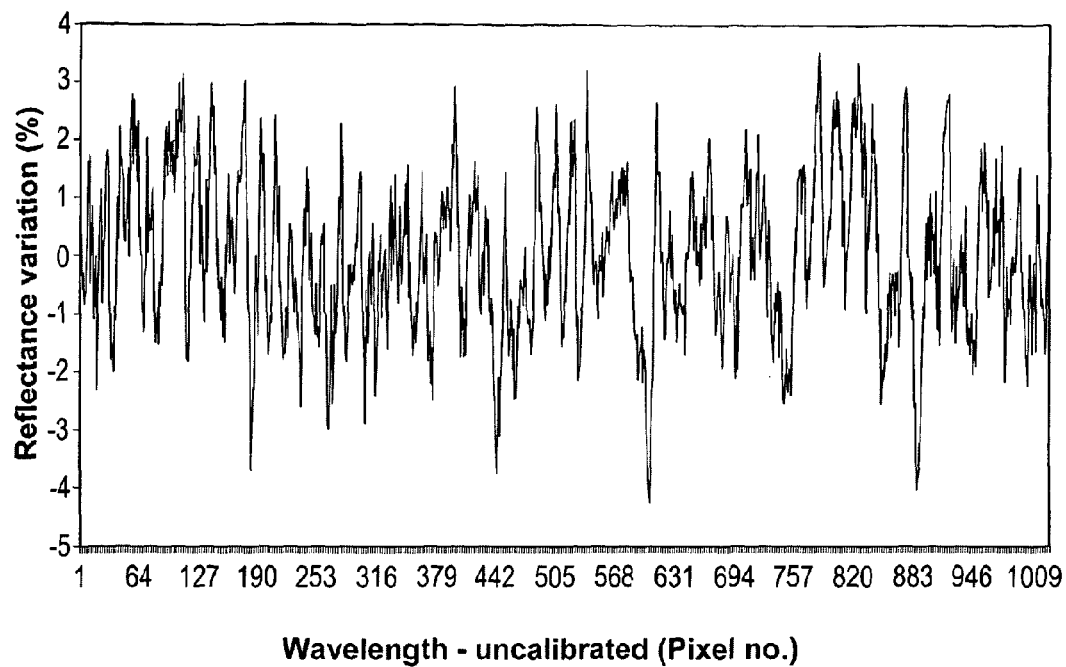
FIG. 2(a) is a spectrum detected from an onion skin using the OCT of FIG. 1.
FIG. 2(b) is an image of the onion skin generated using the spectrum of FIG. 2(a)
Figure 2:

To test the device, an onion was placed with its surface touching the front window. The skin thickness was measured as ~50 μm using an electronic digital caliper. A typical spectrum detected on the spectrometer at the output fiber is shown in FIG. 2a, and the image resulting from the FFT sequence of such reflectance spectra, scanned at 2.5 urn spatial intervals on a 4 mm range, and processed as indicated, is represented in FIG. 2b. The spectrum shows clear interference patterns that translate into the FFT image as a well-defined interface layer, on which both surfaces can be identified, thus confirming the soundness of the measurement layout.

Figure 3:
FIG. 3 is an image of an onion skin taken using the OCT of FIG. 1, but with the front window removed and replaced with a ground glass applied directly on the sample.

In order to assess the self-alignment properties of the setup, the front window was removed and replaced with a 150 μm thick borosilicate glass slide, attached directly to the onion, interposing the index matching gel, thereby cancelling the sample-side surface reflection of the glass. In order to get a direction-insensitive reference (at least for small tilt angles of the optical axis with respect to the surface normal), the back surface of the slide was ground using silicon carbide paper. Under such conditions, the surface appears quasi transparent, and only mildly translucent. Such grinding conditions maintain a well-defined surface position, avoiding positional "blurring" due to excessive roughness. In this configuration, the reference is constituted by the scattering from the ground surface. This is much less critical to align than a direct reflection. The system was then deliberately misaligned avoiding a direct reflection of the back surface into the interferometer, by introducing an approximate 5 degree tilt of the glass slide with respect to the probe optical axis. The resulting image is shown in FIG. 3, from which it can be seen that no image quality is lost. In reducing the reference intensity, this configuration gets closer to a noise-optimal reference intensity.

On the original anti-Newton window system, a circular diaphragm was introduced on the posterior (fiber-side) surface of the 25 mm focusing lens, to vignet the lens, thus reducing the sample-side numerical aperture to 0.035 (and thus lateral resolution). Under such conditions, considering the 1:1.6 throw ratio of the system, the Rayleigh range is extended to 750 μm. Keeping the focus of the system on the front surface of the output window, theory predicts an optical depth of field just short of 800 μm could be expected with a raw lateral resolution of 100 μm (in absence of point-spread function deconvolution), and an axial resolution of the order of 10 μm, limited by the spectrometer spectral bandwidth. Measurements were made to check the practical and theoretical data. The axial resolution of the system was measured by imaging a stack of glass plates 150 μm thick, and was found to be of the order of 10 μm, while the lateral resolution, estimated from the minimum feature size visible on the onion skin, was of the order of 100 μm, in good agreement with the theoretical specifications.

Figure 4:
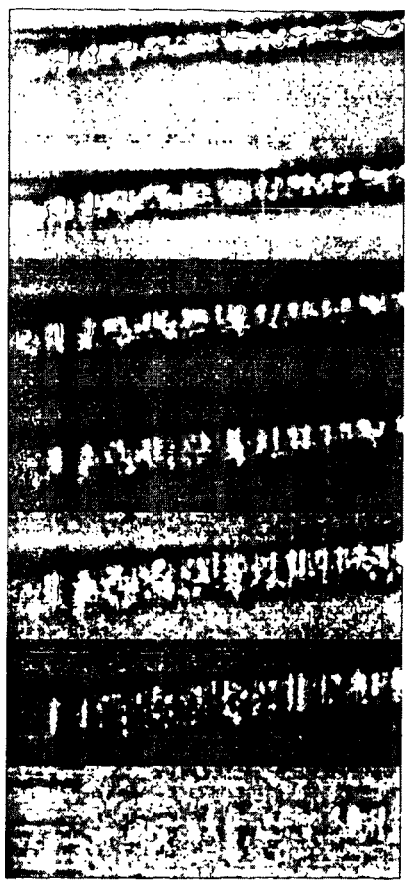
FIG. 4 (a) is an image of an onion skin taken at distances increasing in 150 μm steps from the front window.
Figure 4:
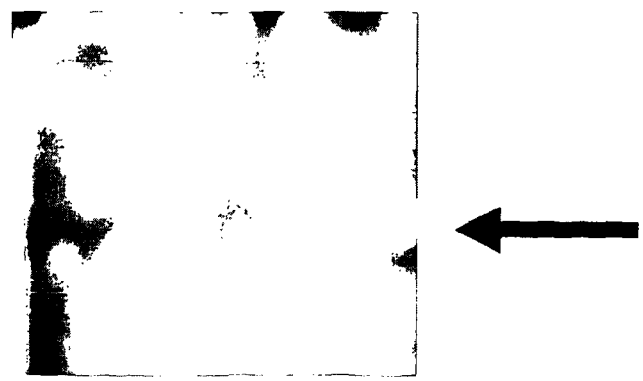

The axial depth of field was measured by imaging the onion directly in contact with the front window, and subsequently translating it away from the window in 150 μm steps. The image sequence, restricted to the surface only, is shown in FIG. 4a. As per the theoretical specifications, a significant loss of detail occurs around a 750 μm distance from the reference window surface, at the Rayleigh range limit, and the image is then rapidly lost, though recoverable up to ~1 mm by heavily increasing the spatial bandpass filtering, with heavy blurring of any feature, see FIG. 4b.

Figure 5:
FIG. 5 is a cross-sectional image of the surface of an ex-vivo cochlea bone.

Cross-sectional images of an ex-vivo human cochlear bone were acquired. A representative example is shown in FIG. 5, where the bone topography is clearly visible up to a 750 μm axial field depth. The result compares well with the literature, thus confirming full system functionality in topographical imaging.

The present invention provides a fiber-based OCT optical configuration, and in particular a Fourier-domain OCT implementation, compatible with a front-looking contact probe. The probe is compact, front-looking, self-referenced, self-aligning, and works in contact with the tissue to be sampled. Tests show that the quality of sample images agrees is consistent with the theoretical performance.

A skilled person will appreciate that variations of the disclosed arrangements are possible without departing from the invention. Accordingly, the above description of the specific embodiment is made by way of example only and not for the purposes of limitation. It will be clear to the skilled person that minor modifications may be made without significant changes to the operation described.

The work leading to this invention has received funding from the Commission of the European Communities Information Society and Media Directorate-General Information and Communication Technologies—Seventh Framework Programme, a Collaborative Project entitled "Array of Robots Augmenting the KiNematics of Endoluminal Surgery" (ARAKNES) ([FP7/2007-2013) under grant agreement no 224565.

The invention claimed is:

1. An optical coherence tomography system comprising a light source, a light detector and a front-facing probe, wherein the probe comprises a window at a front facing end, wherein the window has an inner face that has an anti-reflection surface and allows light from the source to pass through it, and an outer face which is to be positioned in close proximity to, or directly in contact with, a sample to be investigated, wherein the outer face is treated so that some of the light from the source incident upon a region of the outer face is backscattered to thereby form a scattered signal for use as a reference signal and so that some of the light from the source incident upon the same region of the outer face is transmitted to the sample, wherein at least a portion of the light incident upon the sample is backscattered from the sample as a transmitted signal, and wherein the transmitted signal interferes with the reference signal at the light detector.

2. A system as claimed in claim 1 wherein the anti-reflection surface is an anti-Newton surface.

3. A system as claimed in claim 1 wherein the outer face is roughened, thereby to cause backscattering of some of the light from the source to create the scattered signal for use as the reference signal.

4. A system as claimed in claim 1 wherein the scattered signal is small compared to the transmitted signal.

5. A system as claimed in claim 4 wherein the scattered light of the scattered signal is less than 50% of the transmitted light of the transmitted signal.

6. A system as claimed in claim 1 wherein the probe includes one or more optical elements.

7. A system as claimed in claim 6 wherein the optical element comprises at least one focusing means.

8. A system as claimed in claim 7 wherein the focusing means comprises at least one lens.

9. A system as claimed in claim 1 comprising an optical fiber for coupling light into and out of the probe.

10. A system as claimed in claim 9 wherein the end of the fiber is shaped to focus light in the probe.

11. A system as claimed in claim 9 wherein the fiber is treated to avoid or reduce reflections from the end that is coupled with the probe.

12. A system as claimed in claim 11 wherein the fiber end is coated with an anti-reflection material.

13. A system as claimed in claim 9 wherein an anti-reflection window is provided for coupling the fiber end to the probe.

14. A system as claimed in claim 13 wherein the anti-reflection window and fiber are coupled using a glue or an index matching material.

15. A front-facing probe comprising a window at a front facing end, wherein the window has an inner face that has an anti-reflection surface and allows light from a light source to pass through it, and an outer face which is to be positioned in close proximity to, or directly in contact with, a sample to be investigated, wherein the outer face is treated that some of the light from the source incident upon a region of the outer face is backscattered and to thereby form a scattered signal for use as a reference signal and so that some of the light from the source incident upon the same region of the outer face is transmitted to the sample, wherein at least a portion of the light incident upon the sample is backscattered from the sample as a transmitted signal, and wherein the transmitted signal and the reference signal follow a common path to permit interference of the transmitted signal with the reference signal.

16. A probe as claimed in claim 15 wherein the anti-reflection surface is an anti-Newton surface.

17. A probe as claimed in claim 15 wherein the outer face is roughened, thereby to cause backscattering of some of the light from the source to create the scattered signal for use as the reference signal.

18. A probe as claimed in claim 17 wherein the scattered signal is small compared to the transmitted signal.

19. A probe as claimed in claim 18 wherein the scattered light of the scattered signal is less than 50% of the transmitted light of the transmitted signal.

20. A probe as claimed in claim 15 including one or more optical elements.

21. A probe as claimed in claim 20 wherein the optical element comprises at least one focusing means.

22. A probe as claimed in claim 21 wherein the focusing means comprises at least one lens.

23. A probe as claimed in claim 15 wherein an anti-reflection window is provided for coupling a fiber end to the probe.

* * * * *